United States Patent [19]

Burtch

[11] Patent Number: 5,203,701

[45] Date of Patent: Apr. 20, 1993

[54] APPLIANCE FOR TEMPOROMANDIBULAR JOINT DYSFUNCTION

[76] Inventor: David A. Burtch, 182 Coleman Court, Penticton, British Columbia, Canada, V2A 7A9

[21] Appl. No.: 885,341

[22] Filed: May 18, 1992

[51] Int. Cl.⁵ .............................................. A61C 5/00
[52] U.S. Cl. ....................................... 433/215; 433/6; 433/69
[58] Field of Search .............................. 433/6, 69, 215

[56] References Cited

U.S. PATENT DOCUMENTS

| | | | |
|---|---|---|---|
| 1,734,398 | 11/1929 | Phillips | 433/69 |
| 2,618,853 | 11/1952 | Singer et al. | 433/69 |
| 3,068,570 | 12/1962 | Thompson et al. | 433/69 |
| 4,671,766 | 6/1987 | Norton | 433/6 |
| 4,810,192 | 3/1989 | Williams | 433/6 |
| 4,964,769 | 10/1990 | Hass | 433/69 |

FOREIGN PATENT DOCUMENTS

| | | | |
|---|---|---|---|
| 1136450 | 11/1982 | Canada | 433/6 |
| 1147583 | 6/1983 | Canada | 433/215 |
| 1221254 | 5/1987 | Canada | 433/6 |

Primary Examiner—John J. Wilson
Attorney, Agent, or Firm—Dalesman & Company

[57] ABSTRACT

An intraoral appliance to be worn for the diagnosis and treatment of temporomandibular joint dysfunction. The appliance has upper and lower members which fit respectively on the person's maxillary and mandibular arch. The lower member has an upward projection which makes low friction gliding contact against a smooth surface located anteriorly on the upper member. This maintains vertical clearance between the maxillary arch and the mandibular arch and ensures free horizontal movement of the mandible to allow it to assume a position wherein the masticatory muscles are allowed to relax. Wearing the appliance for a period of time relieves the symptoms of acute and/or chronic headaches which result from temporomandibular joint dysfunction.

7 Claims, 3 Drawing Sheets

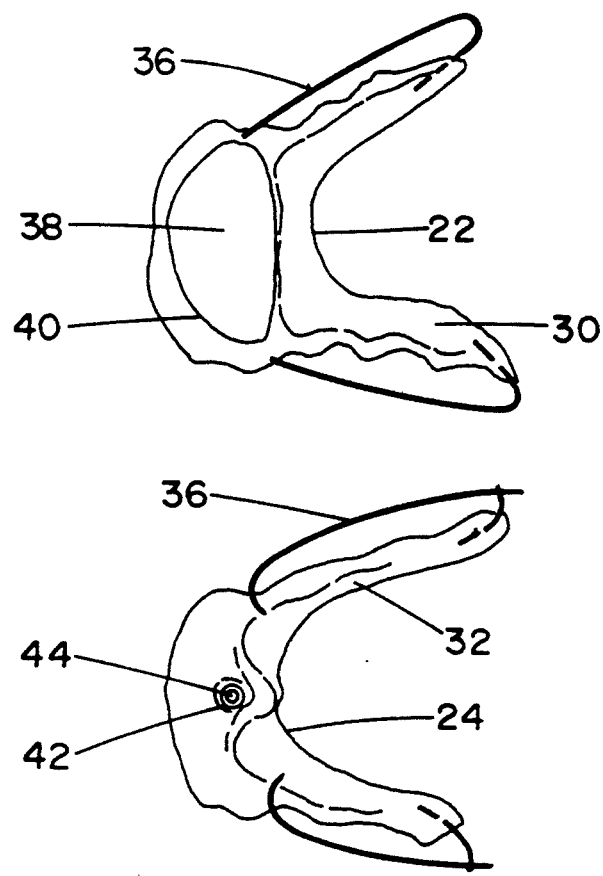
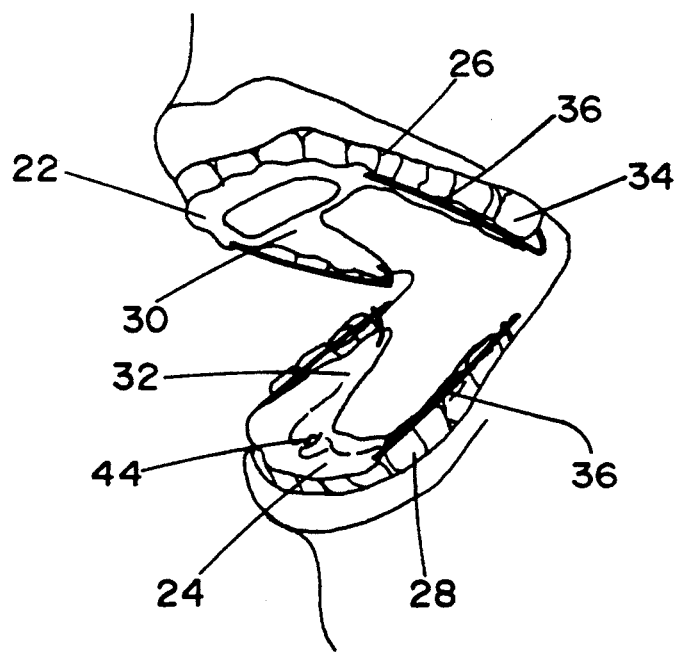
Fig 2
Fig 3

APPLIANCE FOR TEMPOROMANDIBULAR JOINT DYSFUNCTION

BACKGROUND OF THE INVENTION

This invention relates generally to dental appliances and more particularly to an appliance for the diagnosis and treatment of temporomandibular joint dysfunction.

The temporomandibular joints are located on opposite sides of the cranium. On each side, the mandible has a smoothly curved condyle which is received in a matching fossa in the cranium. A meniscus or articular disc is located between the condyle and fossa to provide a cushion between them. Numerous masticatory muscles connect to the mandible to provide for any combination of horizontal and vertical movements relative to the maxilla. It is well known that temporomandibular joint dysfunction is normally caused by malocclusion due to misalignment of the mandible with the maxilla and/or some of the upper and lower teeth. Proprioceptive nerve endings in the periodontal ligaments surrounding the roots of the teeth send messages that control the manner in which the masticatory muscles close the mandible. The primary function of this myo-neural mechanism is to protect the teeth, supporting bone, and soft tissue from the adverse affects of malocclusion. The muscles, while functioning in disharmony, react and bruxism or grinding is initiated in an effort to correct the malocclusion. The result is mild to severe muscle fatigue and in some cases a complete derangement of the temporomandibular joint whereby the articular discs are pulled forward leaving the condyles to function on the retro-discal fibres and the cranial fossae. While temporomandibular joint dysfunction has various symptoms such as neck and ear pain, it usually causes acute and/or chronic headaches which are frequently mistakenly attributed to other causes such as stress or migraine.

Previous attempts to overcome this problem fall into two categories. The first category is appliances which are worn by a person to relieve pain or to reposition the mandible. The second category is devices which are temporarily placed in the mouth of a patient during a dental procedure. An example of the first category is shown in Canadian patent number 1,136,450 to Lerman which issued Nov. 30, 1982 wherein a fluid containing portion of the appliance extends between the upper and lower teeth. Other examples of this category are seen in Canadian patent numbers 1,147,583 to Dufour which issued Jun. 7, 1983, 1,221,254 to Ahlin which issued May 5, 1987 and U.S. Pat. No. 4,671,766 to Norton which issued Jun. 9, 1987 all of which show various appliances to be worn to relocate the mandible to its proper position. Examples of devices in the second category which are used during balancing of dentures or teeth are shown in U.S. Pat. No. 3,068,570 to Thompson et al which issued Dec. 18, 1962 and U.S. Pat. No. 4,964,769 to Hass which issued Oct. 23, 1990. The devices in the second category have the disadvantage that they are not suitable for wear over any extended period of time, while the appliances in the first category have the disadvantages that they are not comfortable to wear and do not satisfactorily relieve the symptoms of temporomandibular joint dysfunction.

SUMMARY OF THE INVENTION

Accordingly, it is an object of the present invention to overcome at least some of the disadvantages of the prior art by providing an intraoral appliance which is worn to maintain clearance between the maxillary arch and the mandibular arch and ensure relatively free horizontal movement of the mandible to relieve the symptoms of temporomandibular joint dysfunction.

To this end, in one of its aspects, the invention provides an intraoral appliance to be worn by a person having a maxilla with a maxillary arch, a mandible with a mandibular arch, and temporomandibular joints which provide for motion of the mandible relative to the maxilla, the appliance comprising an upper member and a separate lower member, the upper member being removably mountable on the maxillary arch, the lower member being removably mountable on the mandibular arch, one of the upper and lower members having an anteriorly located smooth surface facing towards the other of the upper and lower members, the other member having an anteriorly located projection to extend towards the smooth surface of said one member, whereby gliding contact of the projection from said other member against the smooth surface of said one member maintains vertical clearance between the maxillary arch and the mandibular arch and ensures relatively free horizontal movement of the mandible throughout horizontal border movement of the mandible.

Further objects and advantages of the invention will appear from the following description, taken together with the accompanying drawings.

BRIEF DESCRIPTION OF THE DRAWINGS

FIG. 2 is an isometric view of the upper and lower members which form the appliance according to one embodiment of the invention, FIG. 3 is an isometric view showing how appliance is mounted in a person's mouth.

DETAILED DESCRIPTION OF THE INVENTION

Figure 1:
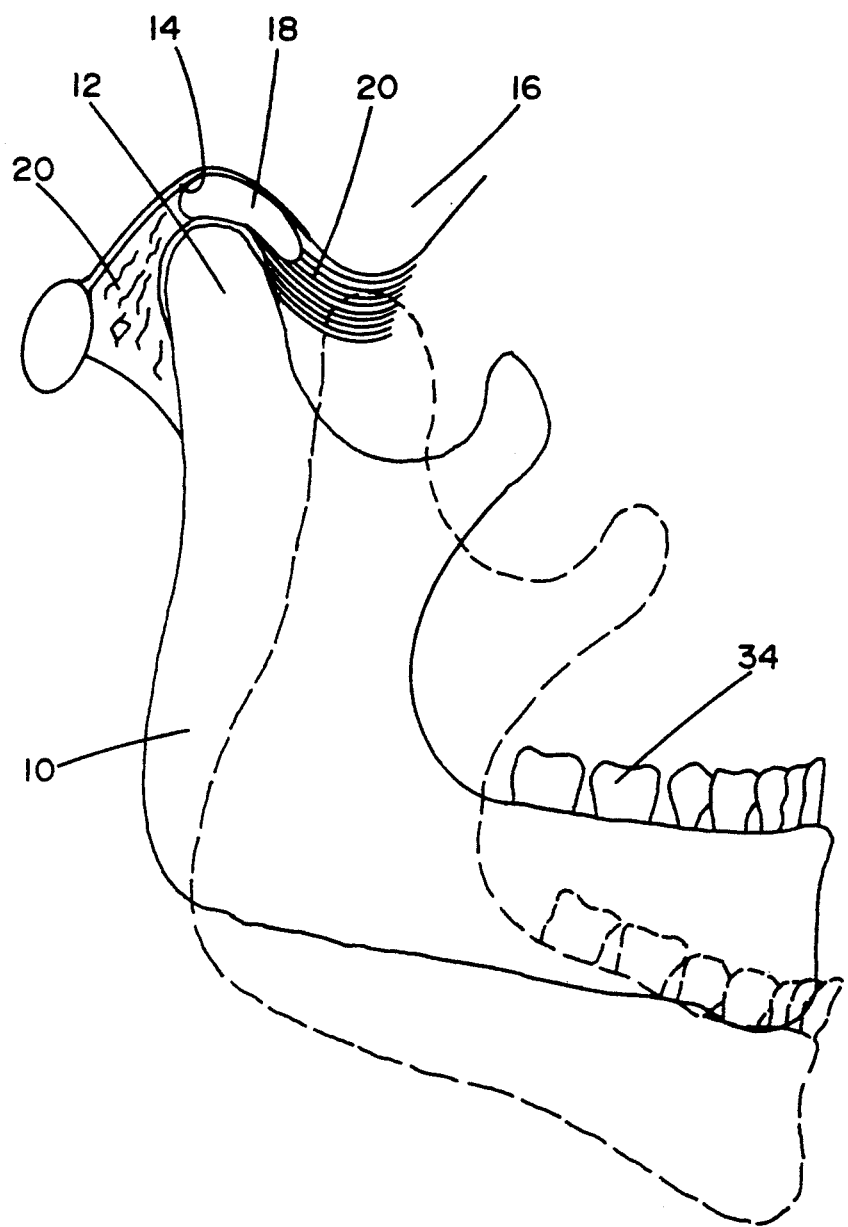
FIG. 1 is a partial side view of the cranium and mandibular arch illustrating one of the temporomandibular joints.

Reference is first made to FIG. 1 which shows the structure of a normal temporomandibular joint in the closed and open (shown dotted) positions. The mandible 10 has a smoothly curved condyle 12 which is received in a matching fossa 14 in the temporal bone 16 of the cranium. A meniscus or articular disc 18 extends between the condyle 12 and the fossa 14 to provide a cushion between them. Numerous masticatory muscles 20 connect to the mandible 10 and to the meniscus 18 to articulate the mandible 10 and to guide the meniscus 18 posteriorly to retain it in position between the condyle 12 and the fossa 14 as the mandible 10 articulates. Of course, there are temporomandibular joints on both sides of the cranium to provide the mandible 10 with the required full range of horizontal as well as vertical movement.

Figure 4:
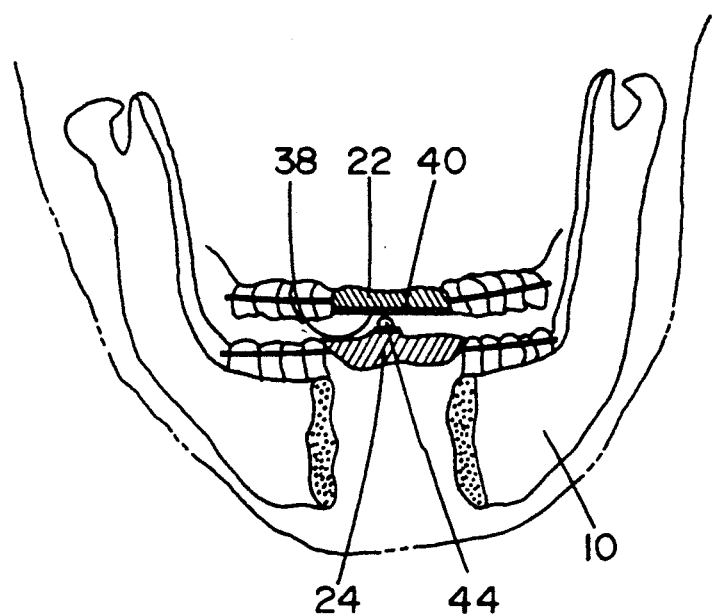
FIG. 4 is a partial sectional view from the front showing the appliance in use in the closed position.

As seen in FIG. 2-4, the intraoral appliance according to a first embodiment of the invention has an upper member 22 and a lower member 24. These members 22, 24 are injection molded of a suitable plastic material and coated with dental acrylic. As seen in FIG. 3, these members 22, 24 are fitted to be removably mounted comfortably on the maxillary and mandibular arches 26, 28 respectively. While the appliance according to the invention can be used with artificial dentures as well as natural teeth, in the embodiment both the upper and lower members 22, 24 have posteriorly extending portions 30, 32 which are fitted along the inner sides of the natural teeth 34. In this case, these portions 30, 32 have retaining wires 36 which are anchored in the plastic and bent to extend across the teeth 34 to keep them in place in the absence of contact between the upper and lower teeth. Of course, other tooth retaining means can be used as well.

The upper member 22 has a smooth glide surface 38 which faces downwardly towards the lower member 24. In this embodiment, the smooth glide surface 38 is provided by a stainless steel plate 40 which is securely embedded in the plastic, but other suitable strong materials or arrangements can be used as well. The smooth glide surface 38 can be flat or slightly curved, and in this embodiment is somewhat concave. However, the surface 38 must be smooth and very resistant to wear. When the upper member 22 is mounted in position, the smooth glide surface 38 is centrally located anteriorly in the maxillary arch 26 to leave sufficient space for the tongue for comfortable wear over an extended period of time.

The lower member 24 has a projection 42 which extends upwards to contact the smooth glide surface 38 of the upper member 22 when the mandible is elevated towards the closed position. The vertical position of the smooth glide surface 38 on the upper member 22 and the height of the projection 42 from the lower member 24 are calculated to ensure vertical clearance between the maxillary arch 26 and the mandibular arch 2 throughout the entire horizontal border movement of the mandible 10. This clearance should not be greater than the freeway space between the closed and relaxed positions of the mandible. In this embodiment, the projection 42 has a ball bearing 44 to provide rolling contact against the smooth glide surface 38 of the upper member 22. However, in other embodiments the projection can have a point made of stainless steel or other suitable configurations and materials to provide low friction gliding contact against the smooth glide surface 38 of the upper member 22. The projection 42 is located to extend centrally near the mid sagittal line in the relaxed position of the mandible 10. The projection 42 is also anteriorly located to contact the smooth glide surface 38 of the upper member 22 when the mandible 10 is elevated towards the closed position which similarly provides a comfortable space for the persons' tongue. The smooth glide surface 38 of the upper member 22 must be of sufficient size and shape to provide for gliding contact of the projection 42 against it throughout the entire horizontal border movement of the mandible. This gliding contact of the projection 42 of the lower member 24 against the smooth glide surface 38 of the upper member 22 must have sufficiently low friction to ensure relatively free horizontal movement of the mandible at all times. In other embodiments, the smooth glide surface 38 can be on the lower member 24 and the projection 42 on the upper member. However, they must be positioned to contact throughout the range of horizontal motion of the mandible to ensure there is clearance between the maxillary arch 26 and the mandibular arch 28.

In use, the appliance is made to fit securely and is mounted (as seen in FIG. 3), in the mouth of a person having the symptoms of temporomandibular joint dysfunction. When the mandible is elevated towards the closed position, the projection 42 on the lower member 24 makes gliding contact against the smooth glide surface 38 on the upper member 22 to maintain clearance between the maxillary arch 26 and the mandibular arch 28 throughout the entire range of movement of the mandible 10. The low friction of the gliding contact between the projection 42 and the smooth glide surface 38 ensures relatively free horizontal movement of the mandible. This allows the mandible to readily assume a normal position wherein the masticatory muscles which control the horizontal movement are relaxed. As the clearance between the teeth is not greater than the freeway space, the mandible elevator muscles are also relaxed in this position. While the appliance is removed during eating, otherwise constant wearing of the appliance for a period of several days will normally considerably alleviate pain and/or headache which are, in fact, the result of temporomandibular joint dysfunction. Thus the appliance can be used to both diagnose temporomandibular joint dysfunction and to treat its symptoms. After the pain has initially been relieved, more intermittent wearing of the appliance such as only when sleeping may be sufficient to satisfactorily relieve the symptoms. The extent of use required varies from person to person depending upon the severity of the condition.

Figure 5A:
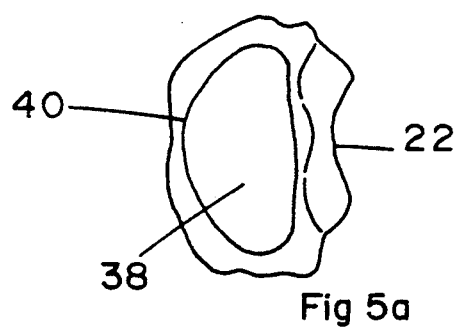
FIG. 5 is an isometric view of the upper and lower members of the appliance according to another embodiment of the invention.
Figure 5B:
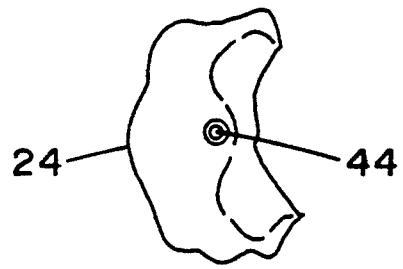

Reference is now made to FIG. 5 which shows a second embodiment of the invention. As can be seen, in this embodiment the appliance is smaller than described above in that the upper and lower members 22, 24 do not have the portions extending posteriorly along the teeth to retain them in place. This embodiment of the appliance is even more comfortable to wear and is used with artificial dentures or for short periods of wear (such as less than two days) with natural teeth where tooth migration is not a concern. Otherwise the structure and use of the upper and lower members 22, 24 with the smooth glide surface 38 and projection 42 is the same as that described above and need not be repeated.

While the description of the appliance has been given with respect to preferred embodiments, it will be evident that various modifications are possible without departing from the scope of the invention as understood by those skilled in the art and as defined in the following claims.

The embodiments of the invention in which an exclusive property or privilege is claimed are defined as follows:

1. An intraoral appliance which is wearable over an extended period of time by a person having a maxilla with a maxillary arch, a mandible with a mandibular arch, and temporomandibular joints which provide for motion of the mandible relative to the maxilla arch, the appliance comprising an upper member and a separate lower member, the upper member being removable mountable on the maxillary arch, the lower member being removably mountable on the mandibular arch, one of the upper and lower members having an anteriorly located smooth surface facing towards the other of the upper and lower members, the other member having an anteriorly located projection to extend towards the smooth surface of said one member, whereby gliding contact of the projection from said other member against the smooth surface of said one member maintains vertical clearance between the maxillary arch and the mandibular arch, the smooth surface of said one member being formed of wear resistant material and the projection from said other member being formed of a material suitable to provide low friction gliding contact against the smooth surface to ensure relatively free horizontal movement of the mandible throughout horizontal border movement of the mandible.

2. An intraoral appliance as claimed in claim 1 wherein the projection from said other member has a ball bearing which contacts the smooth surface of said one member to provide rolling contact between the upper and lower members of the appliance.

3. An intraoral appliance as claimed in claim 2 wherein the smooth surface is on the upper member and the projection is on the lower member.

4. An intraoral appliance as claimed in claim 2 wherein the upper member is molded to fit securely on the maxillary arch, and the lower member is molded to fit securely on the mandibular arch.

5. An intraoral appliance as claimed in claim 4 wherein the clearance maintained between the maxillary arch and the mandibular arch is not substantially greater than the freeway space between the closed and relaxed positions of the mandible.

6. An intraoral appliance as claimed in claim 5 wherein in the relaxed position of the mandible, the projection is near the mid sagittal line of the person.

7. An intraoral appliance as claimed in claim 6 wherein the maxillary arch and the mandibular arch include natural teeth, and each of the upper and lower members have fitted portions extending posteriorly along the respective maxillary arch and mandibular arch to retain the natural teeth in place.

* * * * *